(12) United States Patent
Trouille et al.

(10) Patent No.: US 8,853,169 B2
(45) Date of Patent: *Oct. 7, 2014

(54) C-GLYCOSIDES, USES THEREOF

(75) Inventors: Simon Trouille, Rantigny (FR);
Alexandre Cavezza, Pavillon Sous Bois (FR); Patrick Pichaud, Gif sur Yvette (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/037,106

(22) Filed: Feb. 26, 2008

(65) Prior Publication Data

US 2008/0146516 A1  Jun. 19, 2008

Related U.S. Application Data

(63) Continuation of application No. 11/110,864, filed on Apr. 21, 2005, now Pat. No. 7,358,346.

(60) Provisional application No. 60/567,781, filed on May 5, 2004.

(30) Foreign Application Priority Data

Apr. 23, 2004  (FR) ..................................... 04 50773

(51) Int. Cl.
*A61K 31/70* (2006.01)
*C07H 1/00* (2006.01)
*C07H 15/00* (2006.01)

(52) U.S. Cl.
CPC ..................................... *C07H 15/00* (2013.01)
USPC ........................................... 514/23; 536/1.11

(58) Field of Classification Search
None
See application file for complete search history.

(56) References Cited

U.S. PATENT DOCUMENTS

| | | | |
|---|---|---|---|
| 4,446,312 | A | 5/1984 | Noyori et al. |
| 5,789,385 | A | 8/1998 | Anderson et al. |
| 6,495,147 | B1 | 12/2002 | Dumas et al. |
| 7,049,300 | B2 | 5/2006 | Dalko et al. |

FOREIGN PATENT DOCUMENTS

| | | |
|---|---|---|
| FR | 2 770 776 | 5/1999 |
| WO | WO 02/051803 | 7/2002 |
| WO | WO 02/051828 | 7/2002 |

OTHER PUBLICATIONS

Calwell, "Do single enantiomers have something special to offer", Hum. Psycopharmacol. Cli. Exp. 2001, vol. 16, pp. 67-71.*
Gel-Moreto et al, "Chiral separation of six diastereomeric flavanone-7-glycosides by capillary electrophoresis and analysis of lemon juice", Journal of Chromatography A, vol. 925 (2001), pp. 279-289.*
Haginaka et al, "Separation of Enantiomers on HPLC Chiral Stationary Phases", Enantiomers, vol. 5 (2000), pp. 37-45.*
Fidel J. Lopez-Herrera, et al., "Palytoxin-related C-Glycosides: a Conformational Study Using Molecular Mechanics and an Analysis of Coupling Constants," Tetrahedron: Asymmetry, vol. 1, No. 7, pp. 465-475, 1990.
Wu, Tse Chong et al., "Preferred Conformation of C-Glycosides. 1. Conformational Similiarity of Glycosides and Corresponding C-Glycosides," J. Org. Chem. 1987, 52, (4819-4823), XP002309416.
Solomons "Fundamentals of Organic Chemistry" Third Edition, 1990, pp. 333, 667, 671, 681, 786.
Ault "Techniques and Experiments for Organic Chemistry", Second Edition, 1976, pp. 36-38, 69-70.
Rodrigues, F., et al., "A convenient, one-step, synthesis of β-C-glycosidic ketones in aqueous media," Chem. Commun., 2049-2050 (2000), The Royal Society of Chemistry, Cambridge, England.
Schönenberger, B., et al., "Enantioselective Synthesis of Pseudomonic Acids. I. Synthesis of Key Intermediates," Helvetica Chimica Acta, pp. 2333-2337 (1982), Schweizerische Chemische Gesellschaft, Basel, Switzerland.
Hoffmann, M. G., et al., "Reaktionen von Glycosyltrichloracetimidaten mit silylierten C-Nucelophilen," Liebigs Ann. Chem., pp. 2403-2419 (1985), VCH Verlagsgesellschaft mbH, Weinheim, Germany (English Abstract only).
BeMiller, J. N., et al., "N-Substituted (β-D-galactopyranosyimethyl)amines, and C-β-D-galactopyranosylformamides, and related compounds," Carbohydrate Research, pp. 111-126 (1990), Elsevier Science Publishers B.V., The Netherlands.
Goekjian, P. G., et al. "Preferred Conformation of C-Glycosides. 6. Conformational Similarity of Glycosides and Corresponding C-Glycosides," J. Org. Chem., pp. 6412-6422 (1991), American Chemical Society, USA.

* cited by examiner

*Primary Examiner* — Elli Peselev
(74) *Attorney, Agent, or Firm* — Oblon, Spivak, McClelland, Maier & Neustadt, L.L.P.

(57) ABSTRACT

The present invention relates to novel C-glycoside compounds of given absolute configuration, to a process for synthesizing them and to compositions containing them. The invention also relates to the cosmetic use of these C-glycoside compounds as agents to stimulate the synthesis of glycosaminoglycans containing a D-glucosamine and/or N-acetyl-D-glucosamine residue, advantageously hyaluronic acid, and/or of proteoglycans, advantageously proteoglycans containing hyaluronic acid, by fibroblasts and/or keratinocytes. The invention also relates to a cosmetic process for treating keratin materials using a composition containing at least one C-glycoside compound according to the invention.

12 Claims, No Drawings

C-GLYCOSIDES, USES THEREOF

REFERENCE TO PRIOR APPLICATIONS

This application is a Continuation application of U.S. Ser. No. 11/110,864, filed Apr. 21, 2005; which is a provisional application of U.S. Ser. No. 60/567,781 filed May 5, 2004, and claims priority to French patent application 0450773 filed Apr. 23, 2004.

FIELD OF THE INVENTION

The present invention relates to novel C-glycoside compounds of given absolute configuration, to a process for synthesising them, and to compositions containing them.

The invention also relates to the use of these C-glycoside compounds as agents to stimulate the synthesis of glycosaminoglycans containing a D-glucosamine and/or N-acetyl-D-glucosamine residue, advantageously hyaluronic acid, and/or of proteoglycans, advantageously proteoglycans containing hyaluronic acid, by fibroblasts and/or keratinocytes.

The invention also relates to a process for treating keratin materials using a composition containing at least one C-glycoside compound according to the invention.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Certain C-glycosides compounds have demonstrated beneficial biological properties, in particular for combating ageing of the epidermis, and/or combating drying out of the skin. This is in particular the case with the compounds described in patent application WO-02/051828. These compounds act through stimulating the synthesis of glycosaminoglycans containing a D-glucosamine and/or N-acetyl-D-glucosamine residue, and are represented by formula (F):

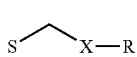
(F)

in which S represents a monosaccharide or a polysaccharide, R represents various linear or cyclic radicals, and the group X can represent a group chosen from: —CO—, —CH(NR₁R₂)—, —CHR'— and —C(=CHR')—, it being possible for R' to represent various radicals, including the hydroxyl radical.

When R' is a hydroxyl radical, the corresponding compound of formula (F) corresponds to formula (F2):

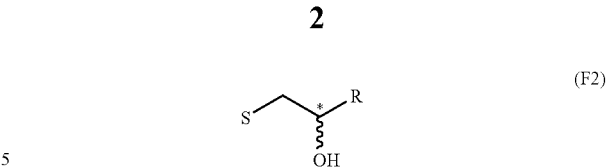

and has an asymmetric carbon, possibly existing in two epimeric forms R and S.

Taking into consideration also the fact that the sugar S can be linked to the side chain via an α or β linkage, the compound that results therefrom, of formula (F3):

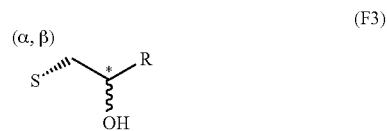

can be in the form of 4 diastereoisomers denoted: (α, S); (α, R); (β, S); and (β, R).

The compounds of formula (F3) have up until now been described in the form of mixtures of several diastereoisomers. In particular, application WO-02/051828 discloses a process of synthesis that makes it possible to produce the compounds in the form of a mixture of diastereoisomers:

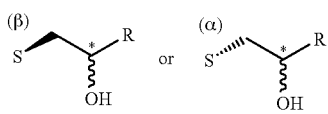

(β, S); (β, R) or (α, S); (α, R)

No method has made it possible to bring about the production of one of the forms in the diastereoisomerically pure state.

SUMMARY OF THE INVENTION

The inventors have discovered that one of the diastereoisomers, (β, S), can be obtained selectively, and studies have shown that it has a biological activity that is much greater than that of the compounds described in the form of a mixture in application WO-02/051828.

DETAILED DESCRIPTION OF THE PREFERRED EMBODIMENTS

The present invention relates to the C-glycoside compound of formula (I):

in which,
S represents a monosaccharide or a polysaccharide comprising up to 20 sugar units, preferably up to 6 sugar units, in pyranose and/or furanose form and of the D series, said mono- or polysaccharide having at least one hydroxyl function that is necessarily free and, optionally, one or more optionally protected amine functions, the linkage

represents a linkage in the β-configuration,

R represents a linear or branched, saturated or unsaturated, alkyl, perfluoroalkyl or hydrofluoroalkyl chain comprising from 1 to 18 carbon atoms, a saturated or unsaturated cycloalkyl, cycloperfluoroalkyl or cyclohydrofluoroalkyl ring comprising from 3 to 11 carbon atoms, or a phenyl or benzyl radical, it being possible for said chain or said ring to be optionally interrupted with one or more hetero atoms chosen from oxygen, sulphur, nitrogen and silicon, and optionally substituted with at least one radical chosen from —OR'$_1$, —SR"$_1$, —NR'''$_1$R'$_2$, —COOR"$_2$, —CONHR'''$_2$, —CN, halogen, perfluoroalkyl or hydrofluoroalkly comprising from 1 to 18 carbon atoms, a cycloalkyl radical comprising from 3 to 11 carbon atoms, an aryl radical or a heterocyclic radical, optionally substituted, R'$_1$, R'$_2$, R"$_1$, R"$_2$, R'''$_1$ and R'''$_2$, which may be identical or different, represent a hydrogen atom, or a radical chosen from a linear or branched, saturated or unsaturated, alkyl, hydroxyl, perfluoroalkyl and/or hydrofluoroalkyl radical comprising from 1 to 30 carbon atoms, and also their physiologically acceptable salts. Mixtures of compounds of formula (I) are of course included. The compounds of formula (I) are preferably in pure form (i.e., no more than 0.1, 0.2, 0.3, 0.4, 0.5, 0.6, 0.7, 0.8 or 0.9% material other than the identified compound(s) of formula (I) present), or substantially pure form (i.e., no more than 1, 3, 5, 10, 12, 15, 18, 20, 25, or 30% material other than the identified compound(s) of formula (I) present), or in a form more pure than that described or obtained in application WO-02/051828. In a preferred embodiment, the weight ratio (×100) of the compound of formula I to the total diastereomeric content (i.e., (β, S)+(β, R) forms) of compounds of formula II:

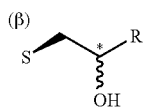

where S and R are as defined in formula I is 100, 99+, 99, 98, 95, 90, 87, 85, 80, 77, 75, and 70, and preferably is greater than 70 and/or greater than that described or obtained in application WO-02/051828.

Compounds of formula (I) are known from the publication "Preferred conformation of C-Glycosides. 1. Conformational similarity of glycosides and corresponding C-glycosides" Tse-Chong Wu, Peter G. Goekjian, Yoshito Kishi, J. Org. Chem., 1987, 52, p 4819-4823: C-β-D-glycopyranoside-2-(S),3-dihydroxypropane (also called 2,6-anhydro-7-deoxy-L-gulononitol) (RN 54548-38-8) and C-β-D-(2-deoxyglycopyranoside)-2-(S),3-dihydroxypropane (also called 4,8-anhydro-3,5-dideoxy-D-glycero-D-gulononitol) (RN 110352-39-1). The novel compounds (referred to as of formula (I)) corresponding to the compounds of formula (I) described above, with the exception of the two compounds mentioned above, are therefore part of the present invention.

An advantageous aspect of the invention concerns the compounds of formula (I) for which S represents a monosaccharide in which the hydroxyl function in the 3-position is free.

Advantageously, the preferred monosaccharides are chosen from D-glucose, D-galactose, D-mannose, D-xylose, D-lyxose, D-glucuronic acid, D-galacturonic acid, D-iduronic acid, N-acetyl-D-glucosamine and N-acetyl-D-galactosamine. Preference will be given most particularly to D-glucose, D-xylose or N-acetyl-D-glucosamine, and very preferably to D-xylose.

Another particular aspect of the invention concerns the compounds of formula (I) for which S represents a polysaccharide as defined above.

Advantageously, the preferred polysaccharides contain up to 6 sugar units, and are chosen from D-maltose, D-lactose, D-cellobiose, D-maltotriose, a disaccharide combining a uronic acid chosen from D-iduronic acid and D-glucuronic acid with a hexosamine chosen from D-galactosamine, D-glucosamine, N-acetyl-D-galactosamine and N-acetyl-D-glucosamine, and an oligosaccharide containing at least one xylose advantageously chosen from xylobiose, methyl-β-xylobioside, xylotriose, xylotetraose, xylopentaose and xylohexaose, and preferably xylobiose, which is made up of two molecules of xylose linked via a 1-4 linkage.

Another particular aspect of the invention concerns the compounds of formula (I) for which R represents a linear or branched, saturated or unsaturated, alkyl, perfluoroalkyl or hydrofluoroalkyl chain comprising from 1 to 6 carbon atoms, a cycloalkyl, cycloperfluoroalkyl or cyclohydrofluoroalkyl ring comprising from 3 to 11 carbon atoms, or a phenyl or benzyl radical, it being possible for said chain or said ring to be optionally interrupted with one or more hetero atoms chosen from oxygen, sulphur, nitrogen and silicon, and optionally substituted with at least one radical chosen from —OR'$_1$, —SR"$_1$, —NR'''$_1$R'$_2$, —COOR"$_2$, —CONHR'''$_2$, —CN, halogen, perfluoroalkyl or hydrofluoroalkyl comprising from 1 to 6 carbon atoms, a cycloalkyl radical comprising from 3 to 11 carbon atoms, an aryl radical or a heterocyclic radical, optionally substituted.

Advantageously, R represents a linear or branched alkyl chain comprising from 1 to 6 carbon atoms or a cycloalkyl ring comprising from 3 to 11 carbon atoms. Preferably, R represents a linear or branched alkyl chain comprising from 1 to 6 carbon atoms, preferably from 1 to 4 carbon atoms, and better still from 1 to 3 carbon atoms, and even better still 1 or 2 carbon atoms.

Among the preferred alkyl groups, mention may be made of methyl, ethyl, propyl, isopropyl, butyl, isobutyl or tert-butyl groups, and preferably a methyl group.

The aryl groups that are preferred for implementing the invention are phenyl and naphthyl groups.

Among the heterocyclic groups that are preferred for implementing the present invention, mention may be made of furyl, thienyl, pyrazolyl, imidazolyl, pyridyl and pyrimidyl groups.

Among the C-glycoside compounds of formula (I), preference is given most particularly to the C-β-D-xylopyranoside-2-(S)-hydroxypropane of formula:

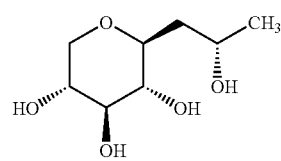

and the C-β-D-fucopyranoside-2-(S)-hydroxypropane of formula:

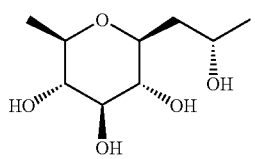

The present invention also relates to a process for preparing the compounds of formula (I) as defined above. This preparation process makes it possible to obtain the compounds of formula (I) selectively, in the form of a single diastereoisomer (β, S).

The starting compound for the synthesis of the compound of formula (I) is the corresponding carbonylated compound of formula (II):

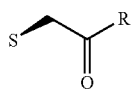

in which S and R have the same meaning as above, and

represents a linkage in the β-configuration.

It is theoretically possible to carry out the reduction of the compound (II) by known methods. Conventional reducing agents can be used, for instance:
- aluminium hydrides and their salts (in particular their lithium, potassium or sodium salts), and also their compounds such as, for example, Red-Al (sodium bis(2-methoxyethoxy)aluminiumhydride) or DIBAL-H (diisobutylaluminium hydride),
- borohydrides and their salts (in particular their lithium, potassium or sodium salts), and also their compounds such as, for example, L-selectride or K-selectride (lithium triisobutylborohydride or potassium triisobutylborohydride, respectively),
- metals (for example sodium, potassium or lithium),
- catalytic hydrogenation in the presence of conventional catalysts such as platinum or palladium-on-charcoal.

The solvents conventionally used to carry out these reduction reactions are preferably chosen from linear or branched primary, secondary or tertiary alcohols containing between 1 and 8 carbon atoms (for example methanol, ethanol, isopropanol or tert-butanol), linear or cyclic ethers (for example ethyl ether, dioxane or tetrahydrofuran), aromatic compounds such as toluene, liquid ammonia, and water.

These processes for synthesis described in the prior art result however in a mixture of two diastereoisomeric forms in varying proportions, starting with a single compound of formula (II) of fixed absolute configuration. This is in particular the case with the process described in application WO-02/051828.

The inventors have discovered, surprisingly, that the choice of a specific reducing agent and of a particular solvent, used in the presence of an organic acid, makes it possible to produce a compound of formula (I) defined above, in the form of a single diastereoisomer (β, S), which can in particular be obtained without resorting to separation of the diastereoisomers.

The invention therefore relates to the process for preparing a compound of formula (I), as defined above, by reacting a compound of formula (II):

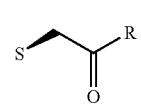

in which S and R have the same meaning as above, in solution in a linear, branched or cyclic secondary alcohol containing from 3 to 8 carbon atoms, with a reducing agent comprising: (a) a metal borohydride of formula $MBH_4$ in which M represents an alkaline metal, in the presence of an organic carboxylic or sulphonic acid containing from 1 to 10 carbon atoms, or (b) a reactive species or complex formed by the association of a metal borohydride with an organic acid and, optionally, a secondary alcohol.

In an advantageous aspect of the invention, the secondary alcohol used in the process above is isopropanol.

Another advantageous aspect of the invention concerns a preparation process as described above, in which the metal borohydride is chosen from sodium borohydride, lithium borohydride or potassium borohydride, and more particularly sodium borohydride.

The organic carboxylic acids that are suitable for implementing the present invention may in particular be chosen from aliphatic acids having from 1 to 10 carbon atoms, more particularly acetic acid, propanoic acid or butanoic acid, and aromatic acids having in particular from 6 to 10 carbon atoms, in particular benzoic acid.

The organic sulphonic acids that are suitable for implementing the present invention are advantageously chosen from aliphatic acids having from 1 to 10 carbon atoms, more particularly methanesulphonic acid or trifluoromethanesulphonic acid, and aromatic acids having in particular from 6 to 10 carbon atoms, in particular para-toluenesulphonic acid.

The preferred organic acid for implementing the process for preparing the compounds of formula (I) as defined above is acetic acid.

Alternatively and particularly effectively, the reduction of the compound of formula (II) as defined above can be carried out, when it is available, by means of the reactive species or complex formed by the association of the metal borohydride with the organic acid and, optionally, secondary alcohol. Mention may in particular be made of sodium triacetoxyborohydride of formula $NaBH(OAc)_3$, which corresponds to the association of one molar equivalent of sodium borohydride with 3 molar equivalents of acetic acid.

In an advantageous aspect of the invention, the molar ratio of the organic acid to the metal borohydride used in the process above is at least 3.

In another preferred aspect of the invention, the ratio of the secondary alcohol to the organic acid ranges between 1/4 and 20/1 by volume, and will advantageously be adjusted to a value equal to 9/2 by volume.

Preferred compounds of formula (II) for implementing the preparation process according to the present invention include the C-β-D-xylopyranoside-2-propanone of formula:

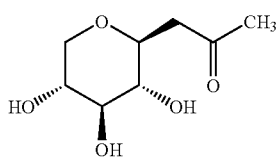

and the C-β-D-fucopyranoside-2-propanone of formula:

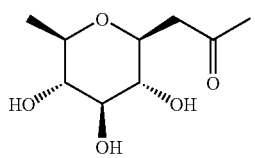

Another subject of the invention concerns compositions which comprise at least one C-glycoside compound corresponding to formula (I) as defined above and a physiologically acceptable medium. In particular, the composition is suitable for topical application to the skin. The physiologically acceptable medium will preferably be a cosmetically acceptable medium, i.e. one which has no unpleasant odour, colour or appearance, and which does not generate any stinging, tightness or redness that is unacceptable to the user.

The composition according to the invention can comprise these C-glycoside compounds alone or as a mixture in any proportion.

The term "physiologically acceptable medium" is understood to mean a medium that is compatible with the keratin materials of human beings, such as the skin, the mucous membranes, the nails, the scalp and/or the hair.

The amount of C-glycoside compound(s) corresponding to formula (I) that can be used in the compositions according to the invention depends, of course, on the desired effect and should preferably be in an amount that is effective for stimulating the synthesis of hyaluronic acid and of proteoglycans (PCs) by fibroblasts and keratinocytes.

To give an order of magnitude, the composition according to the invention can contain at least one C-glycoside compound corresponding to formula (I) in an amount representing from 0.00001% to 25% of the total weight of the composition, and preferably in an amount representing from 0.0001% to 10% of the total weight of the composition.

The composition according to the invention can be used for cosmetic or pharmaceutical, particularly dermatological, application. Preferably, the composition according to the invention is intended for cosmetic application.

Advantageously, the compositions according to the invention are preferably care compositions and/or antisun compositions and/or washing compositions and/or make-up compositions and/or make-up-removing compositions for the skin of the body and/or of the face and/or for the mucous membranes (for example the lips) and/or for the scalp and/or for the hair and/or for the nails and/or for the eyelashes and/or for the eyebrows.

Another subject of the invention also relates to the use of the composition as defined above, for cosmetically treating and/or making up keratin materials, such as the hair, the skin, in particular the skin of the body and/or the face, the eyelashes, the eyebrows, the nails or the mucous membranes.

Another subject of the invention relates to the use of the composition as defined above, for improving the appearance of keratin materials.

The composition according to the invention can be ingested, injected or applied to the skin (on any area of the skin of the body), the hair, the nails or the mucous membranes (buccal, jugal, gingival, genital or conjunctival mucous membranes).

The composition according to the invention may be in any form for example in any of the pharmaceutical forms normally used for topical application, in particular in the form of an aqueous, aqueous-alcoholic or oily solution, of an oil-in-water or a water-in-oil or multiple emulsion, of an aqueous or oily gel, of a liquid, pasty or solid anhydrous product, or of a dispersion of oil in an aqueous phase by means of spherules, it being possible for these spherules to be polymeric nanoparticles such as nanospheres and nanocapsules, or better still lipid vesicles of the ionic and/or non-ionic type. These compositions are prepared according to the usual methods.

This composition may be more or less fluid and may have the appearance of a white or coloured cream, of an ointment, of a milk, of a lotion, of a serum, of a paste or of a mousse. It may optionally be applied to the skin in the form of an aerosol. It may also be in solid form, and for example in the form of a stick.

The composition of the invention can be used as a haircare composition, and in particular a shampoo, a hairsetting lotion, a medicated lotion, a styling cream or gel, a dye composition (in particular an oxidation dye composition) optionally in the form of a dyeing shampoo, a hair-restructuring lotion, a permanent-waving composition (in particular a composition for the first step of a permanent wave), a lotion or a gel for preventing hair loss, an antiparasitic shampoo, etc.

When the composition according to the invention is an emulsion, the proportion of the fatty phase can for example range from 5% to 80% by weight, and preferably from 5% to 50% by weight relative to the total weight of the composition. The oils, the waxes, the emulsifiers and the coemulsifiers used in the composition in the form of an emulsion are chosen from those conventionally used in the cosmetics field. The emulsifier and the coemulsifier are preferably present in the composition in a proportion ranging from 0.3% to 30% by weight, and more preferably from 0.5% to 20% by weight relative to the total weight of the composition. The emulsion may also contain lipid vesicles.

The compositions of the invention may also contain adjuvants from, for example, the cosmetics and dermatological fields, such as hydrophilic or lipophilic gelling agents, hydrophilic or lipophilic active agents, preserving agents, antioxidants, solvents, fragrances, fillers, screening agents, pigments, chelating agents, odour absorbers and dyestuffs. The amounts of these various adjuvants are not limited and may be those conventionally used in the fields under consideration, and for example from 0.01% to 20% of the total weight of the composition. These adjuvants, depending on their nature, can be introduced into the fatty phase, into the aqueous phase, into the lipid vesicules and/or into the nanoparticles.

As oils or waxes that can be used in the invention, mention may be made of mineral oils (liquid petroleum jelly), plant oils (liquid fraction of karite butter, sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) can be added to these oils.

As emulsifiers and coemulsifiers that can be used in the invention, mention may be made, for example, of fatty acids esters of polyethylene glycol, such as PEG-40 stearate and PEG-100 stearate, fatty acid esters of polyols, such as glyceryl stearate and sorbitan tristearate.

As hydrophilic gelling agents that can be used in the invention, mention may be made for example of carboxyvinyl polymers (carbomer), acrylic copolymers such as acrylate/alkylacrylate copolymers, polyacrylamides, polysaccharides such as hydroxypropyl-cellulose, natural gums and clays, and as lipophilic gelling agents, mention may be made of modified clays, for instance bentones, metal salts of fatty acids, for instance aluminium stearates, and hydrophobic silica.

As active agents, the composition according to the invention may comprise for example at least one compound chosen from: desquamating agents, humectants, emollients, agents for increasing keratinocyte differentiation, and mixtures thereof.

The C-glycoside compounds corresponding to formula (I) exhibit notable activities of stimulating the synthesis of glycosaminoglycans (GAGs) containing a D-glucosamine and/or N-acetyl-D-glucosamine residue, advantageously hyaluronic acid, and/or of proteoglycans (PGs), advantageously PGs containing hyaluronic acid, by fibroblasts and/or keratinocytes.

Thus, the present invention also relates to the cosmetic use of at least one compound of formula (I) as defined above, as an agent to stimulate the synthesis of glycosaminoglycans containing a D-glucosamine and/or N-acetyl-D-glucosamine residue, and/or of proteoglycans, by fibroblasts and/or keratinocytes.

Another aspect of the invention relates to the cosmetic use of at least one compound of formula (I) as defined above, as an agent intended to stimulate the synthesis of hyaluronic acid and/or of proteoglycans containing hyaluronic acid.

More precisely, it has become apparent that the C-glycoside compounds of formula (I), due to their stimulatory effect on the synthesis of GAGs containing a D-glucosamine and/or N-acetyl-D-glucosamine residue, advantageously hyaluronic acid, and/or of PGs, advantageously of PGs containing hyaluronic acid by fibroblasts and/or keratinocytes, make it possible:

to combat ageing of the epidermis. It is in fact known that ageing of the epidermis is, to a large extent, linked to a loss of hyaluronic acid, to maintain and/or stimulate moisturization and/or to combat the drying out of the skin linked to an insufficiency of the action of GAGs, in particular of hyaluronic acid. Such drying out is observed in particular on aged skin and is essentially linked to a loss of hyaluronic acid, to improve the tonicity of the skin. It has in fact been observed that increasing the synthesis of PGs and of GAGs makes it possible to create a hydrated cellular environment that is favourable to exchanges of nutrients, of ions, of cytokine and of growth factors secreted by epidermal cells. Such an environment is also favourable to the elimination of toxic metabolites. This effect is thus reflected by healthy tonic skin, to maintain or restore the suppleness and elasticity of the skin. This effect is associated with stimulating the synthesis of PGs and of GAGs, which makes it possible to create a hydrated environment for the matrix constituents, in particular at the dermo-epidermal junction, to promote micro-displacements between the components of this matrix during mechanical stress. Such an effect therefore contributes to making the skin more supple and more elastic, to improve the mineralization of the epidermis, thus making the skin healthier and improving its vitality. This effect is associated with improving the synthesis of GAGs, which makes it possible to ensure good mineralization of the epidermis. In fact, GAGs can bind ions, via their charge groups, and can contribute to the osmolarity of the epidermis. In this case also, good mineralization of the skin is synonymous with healthy skin showing good vitality, to facilitate intercellular exchanges. This effect is also related to stimulating the synthesis of GAGs, which makes it possible to ensure correct differentiation of the epidermis since a destruction of hyaluronic acid gives rise to an opening of the intercellular spaces and epidermal acanthosis.

This effect makes it possible to obtain skin that is more tonic, denser and more compact, to improve the three-dimensional structure of the dermo-epidermal junction. This is also related to improving the synthesis of PGs and of GAGs, which makes it possible to ensure the spatial organization of the matrix constituents by reinforcing, for example at the dermo-epidermal junction, the binding between laminin-6 and nidogen (nidogen is a glycoprotein which, with laminin, attaches endothelial cells to type IV collagen), to combat chapping and the cracked appearance of the skin, to facilitate the migration of keratinocytes, allowing the formation of a horny layer of good quality, to modulate the action of the growth factors and cytokines produced by the skin cells. Such an effect affords the cells the signals they need to carry out their function.

The present invention therefore also relates to processes for accomplishing, providing, etc. the above-noted benefits, comprising applying the compound(s) and or composition(s) of the invention to skin, and especially to skin in need of such treatment and for such purpose. Such processes include one for combating ageing of the skin, comprising the application to the epidermis of a composition containing at least one compound of formula (I) as defined above.

The invention also relates to a cosmetic process for maintaining and/or stimulating the moisturization of the skin, comprising the application to the skin of a composition containing at least one compound of formula (I) as defined above.

The invention also relates to a cosmetic process for combating the drying out of the skin linked to the insufficiency of the action of GAGs containing a D-glucosamine and/or N-acetyl-glucosamine residue, in particular hyaluronic acid, comprising the application to the skin of a composition containing at least one compound of formula (I) as defined above.

The invention also relates to a cosmetic process for maintaining and/or restoring the suppleness and the elasticity of the skin, comprising the application to the epidermis of a composition containing at least one compound of formula (I) as defined above.

Finally, the invention relates to a cosmetic process for combating chapping and/or the cracked appearance of the skin, comprising the application to the skin of a composition containing at least one compound of formula (I) as defined above.

In the dermatological field, the compounds according to the invention facilitate cicatrization without scar formation, thus making it possible to repair epidermal microtraumas which appear when the continuity of the skin is broken.

A subject of the invention is therefore also the use of at least one compound of formula (I) as defined above, for producing a dermatological composition to promote skin cicatrization.

The examples which follow illustrate the invention without limiting the scope thereof. The compounds are, depending on the case, given as chemical names or as CTFA (International Cosmetic Ingredient Dictionary and Handbook) names. The proportions are given as percentages by weight, unless otherwise indicated.

Example 1

Production of C-β-D-xylopyranoside-2-(S)-hydroxypropane 2 ml of acetic acid, followed rapidly by 120 mg (1.2 eq.) of sodium borohydride as granules were added to a solution of 500 mg of C-β-D-xylopyranoside-2-propanone (described in Example 1 of application WO-02/051828) in 9 ml of isopropanol. The medium was left at ambient temperature for 30 minutes with stirring. 120 mg (1.2 eq.) of sodium borohydride as granules were then added. The reaction medium was left for 1 hour at ambient temperature with stirring. 10 ml of acetone were then added and, after stirring for 30 minutes at ambient temperature, the reaction medium was concentrated under vacuum. The residue obtained was purified by silica gel chromatography so as to selectively produce the expected compound C-β-D-xylopyranoside-2-(S)-hydroxypropane with a 95% yield.

Physico Chemical Characteristics of the Compound:

Melting point: 120-122° C.

Optical rotation: −37° (at 20° C. in methanol, and at a concentration [C]=1 g/100 ml)

$^1$H NMR: 1.03 (t, 3H); 1.46 (m, 1H); 1.71 (m, 1H); 2.85 (m, 1H); 2.94 (m, 1H); 2.99 (m, 2H); 3.24 (m, 1H); 3.67 (m, 1H); 3.77 (m, 1H).

Structure confirmed by X-ray diffraction.

Example 2

Production of C-β-D-xylopyranoside-2-(S)-hydroxypropane

The expected compound was obtained according the process described in Example 1, replacing the 2 ml of acetic acid and the sodium borohydride with two times 1.2 equivalents of sodium triacetoxyborohydride (NaBH(OAc)$_3$).

The product was obtained with a quantitative yield, and selectively in (β, S) form. The physico chemical characteristics are identical in all respects to those obtained in Example 1.

Example 3

Study of the Effect of C-Glycoside Compounds According to the Invention on the Synthesis of Hyaluronic Acid The study was carried out by measuring the incorporation of radioactive glucosamine into the matrix neosynthesized by normal human dermal fibroblast cultures. The incorporation of radioactive glucosamine indicates specific neosynthesis of glycosaminoglycans via incorporation of the sulphated form of this glucosamine.

Normal human dermal fibroblasts were seeded in the conventional culture medium and were then preincubated for 24 hours. The culture medium was then replaced with the test compounds at concentrations of 0.3, 1 and 3 mM; or culture medium (control); or TGFβ at 10 ng/ml (quality control). The cells were incubated for 72 hours with the addition of $^{35}$S-sulphate during the final 24 hours of culture. The GAGs in the matrix were extracted with a chaotropic buffer and then purified by ion exchange chromatography (adsorption of the anionic molecules onto Q-sepharose beads under high stringency conditions, followed by desorption of the weakly and moderately anionic molecules with urea). The radioactivity incorporated into the very cationic molecules that remained on the support were counted by liquid scintillation.

The results are expressed as percentage relative to the control:

| Compound tested | Concentration | cpm | sd | n | %/control | p |
|---|---|---|---|---|---|---|
| Control | — | 5010 | 543 | 6 | 100 | — |
| TGFβ | 10 ng/ml | 9625 | 1137 | 6 | 192 | p < 0.01 |
| Comparative example* | 3 mM | 31735 | 799 | 3 | 633 | p < 0.01 |
|  | 1 mM | 20620 | 1969 | 3 | 412 | p < 0.01 |
|  | 0.3 mM | 10678 | 748 | 3 | 213 | p < 0.01 |
| Example 1 | 3 mM | 40770 | 1613 | 3 | 814 | p < 0.01 |
|  | 1 mM | 30943 | 588 | 3 | 618 | p < 0.01 |
|  | 0.3 mM | 16276 | 1195 | 3 | 325 | p < 0.01 |

*The comparative example is the compound described in Example 4 of application WO-02/051828, in the form of a racemic mixture (β, S) (β, R).

The values measured are given in counts per minute (cpm)

sd: standard deviation p: confidence interval n: replicates

These results indicate that the compounds of formula (I) of the present invention having a (β, S) conformation stimulate the neosynthesis of GAGs to a much greater extent than the stimulation obtained with the compounds of the prior that are in the form of a mixture, thus showing the superiority of one of the two diastereoisomers over the other.

Example 4

Preparation of C-β-D-fucopyranoside-2-(S)-hydroxypropane a) Preparation of C-β-D-fucopyranoside-2-propanone

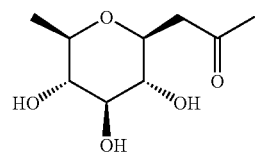

2 g of D-fucose was dissolved in 20 ml of water, in a 50 ml three-necked flask equipped with a condenser, a thermometer and magnetic stirring, and then penta-2,4-dione (1.51 g, 1.2 eq) and sodium bicarbonate (1.53 g, 1.5 eq) were added. The mixture was stirred for 18 hours at 90° C. The reaction medium was then washed with dichloromethane and concentrated under vacuum. The brown oil obtained was purified by silica gel chromatography so as to produce the expected compound C-β-D-fucopyranoside-2-propanone with a 92% yield (2.3 g).

Mass spectometry is in conformity.

b) Production of
C-β-D-fucopyranoside-2-(S)-hydroxypropane

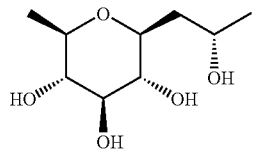

7.5 ml of acetic acid, followed rapidly by 510 mg (1.2 eq.) of sodium borohydride as granules, were added to a solution of 2.3 g of C-β-D-fucopyranoside-2-propanone in 33 ml of isopropanol. The medium was left at ambient temperature for 30 minutes with stirring. 510 mg (1.2 eq.) of sodium borohydride as granules are then added. The reaction medium was left for 8 hours at ambient temperature with stirring. 10 ml of acetone are then added and, after stirring at ambient temperature for 12 hours, the reaction medium was concentrated under vacuum. The residue obtained was purified by silica gel chromatography so as to selectively produce the expected compound C-β-D-fucopyranoside-2-(S)-hydroxypropane with a 65% yield.

NMR (500 MHz) and mass spectrometry are in conformity with the expected product.

Example 5

Compositions According to the Invention

The following compositions are prepared according to known processes:

Composition 1: Oil-in-Water (O/W) Cream

| | |
|---|---|
| Glyceryl monostearate | 6.0% |
| Stearyl alcohol | 4.0% |
| Liquid petroleum jelly | 10.0% |
| Silicone oil | 5.0% |
| C-β-D-Xylopyranoside-2-(S)-hydroxypropane | 10.0% |
| Glycerol | 8.0% |
| Carboxyvinyl polymer of the Carbopol type | 0.3% |
| Preserving agents | 0.4% |
| Fragrance | 0.5% |
| Triethanolamine | 0.3% |
| Water qs | 100% |

Composition 2: Water-in-Oil (W/O) Cream

| | |
|---|---|
| Octyl dodecanol | 10.0% |
| Magnesium stearate | 4.0% |
| Natural beeswax | 5.0% |
| Sorbitan sesquioleate | 4.5% |
| Glyceryl mono- and distearate and potassium stearate | 1.0% |
| Liquid petroleum jelly | 22.0% |
| Jojoba oil | 4.0% |
| C-β-D-Xylopyranoside-2-(S)-hydroxypropane | 2.5% |
| Preserving agent | 0.4% |
| Fragrance | 0.6% |
| Water qs | 100% |

Composition 3: Oil-in-Water (O/W) Cream

| | |
|---|---|
| Glyceryl monostearate | 6.0% |
| Stearyl alcohol | 4.0% |
| Liquid petroleum jelly | 10.0% |
| Silicone oil | 5.0% |
| C-β-D-Fucopyranoside-2-(S)-hydroxypropane | 10.0% |
| Glycerol | 8.0% |
| Carboxyvinyl polymer of the Carbopol type | 0.3% |
| Preserving agents | 0.4% |
| Fragrance | 0.5% |
| Triethanolamine | 0.3% |
| Water qs | 100% |

The above written description of the invention provides a manner and process of making and using it such that any person skilled in this art is enabled to make and use the same, this enablement being provided in particular for the subject matter of the appended claims, which make up a part of the original description.

In this regard, the following embodiments make out preferred aspects of the invention:

The composition according to the invention, wherein, for the compound of formula (I), the group R represents a linear or branched alkyl chain comprising from 1 to 18 carbon atoms.

The composition according to the invention, wherein, for the compound of formula (I), S represents a monosaccharide having at least one hydroxyl function that is free and, optionally, one or more optionally protected amine functions.

The composition according to the invention, wherein, for the compound of formula (I), S represents a monosaccharide in which the hydroxyl function in the 3-position is free.

The composition according to the invention, wherein, for the compound of formula (I), S represents a monosaccharide chosen from D-glucose, D-galactose, D-mannose, D-xylose, D-lyxose, D-glucuronic acid, D-galacturonic acid, D-iduronic acid, N-acetyl-D-glucosamine and N-acetyl-D-galactosamine.

The composition according to the invention, wherein, for the compound of formula (I), S represents a D-xylose residue.

The composition according to the invention, comprising C-β-D-xylopyranoside-2-(S)-hydroxypropane and/or C-β-D-fucopyranoside-2-(S)-hydroxypropane.

The composition according to the invention, wherein said composition is suitable for topical application to the skin.

The composition according to the invention, wherein the physiologically acceptable medium is a cosmetically acceptable medium.

The composition according to the invention, wherein the compound of formula (I) is present in an amount ranging from 0.00001% to 25% by weight relative to the total weight of the composition.

The composition according to the invention, wherein the compound of formula (I) is present in an amount ranging from 0.0001% to 10% by weight relative to the total weight of the composition.

A process for combating signs of ageing of the skin, comprising the application to the epidermis of a composition comprising at least one compound of formula (I) as defined in the invention.

Cosmetic process for maintaining and/or stimulating the moisturization of the skin, comprising the application to skin in need thereof of a composition comprising at least one compound of formula (I) as defined in the invention.

A cosmetic process for combating the drying out of the skin linked to the insufficiency of the action of GAGs containing a D-glucosamine and/or N-acetyl-glucosamine residue, comprising the application to skin in need thereof of a composition comprising at least one compound of formula (I) as defined in the invention.

A cosmetic process for maintaining and/or restoring the suppleness and elasticity of the skin, comprising the application to the epidermis of a composition comprising at least one compound of formula (I) as defined in the invention.

A cosmetic process for combating chapping and/or the cracked appearance of the skin, comprising the application to skin in need thereof of a composition comprising at least one compound of formula (I) as defined in the invention.

A method for promoting skin cicatrisation comprising the application of a composition comprising at least one compound of formula (I) as defined in the invention to skin in need thereof.

A method for stimulating the synthesis of glycosaminoglycans containing a D-glucosamine and/or N-acetyl-D-glucosamine residue, and/or of proteoglycans, by fibroblasts and/or keratinocytes comprising the application of a composition comprising at least one compound of formula (I) as defined in the invention to skin in need thereof.

A method for stimulating the synthesis of hyaluronic acid and/or of proteoglycans containing hyaluronic acid comprising the application of a composition comprising at least one compound of formula (I) as defined in the invention to skin in need thereof.

As used herein, the phrases "selected from the group consisting of," "chosen from," and the like include mixtures of the specified materials.

Formula (I) compares to formula (I'):

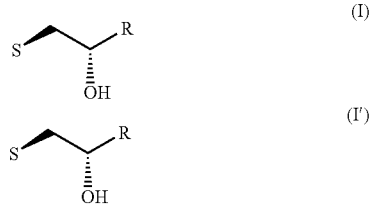

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A (β, S) C-glycoside compound of formula (I') that is at least 90% pure, which is C-β-D-xylopyranoside-2-(S)-hydroxypropane or C-β-D-fucopyranoside-2-(S)-hydroxypropane.

2. A composition comprising, in a physiologically acceptable medium, at least one compound according to claim 1.

3. The compound of according to claim 1, which is C-β-D-xylopyranoside-2-(S)-hydroxypropane.

4. The composition according to claim 2, wherein the compound is C-β-D-xylopyranoside-2-(S)-hydroxypropane.

5. The compound according to claim 1, which is at least 95% pure.

6. The compound according to claim 1, which is at least 97% pure.

7. The composition according to claim 2, wherein the compound is at least 95% pure.

8. The composition according to claim 2, wherein the compound is at least 97% pure.

9. The compound according to claim 3, which is at least 95% pure.

10. The compound according to claim 3, which is at least 97% pure.

11. The composition according to claim 4, wherein the compound is at least 95% pure.

12. The composition according to claim 4, wherein the compound is at least 97% pure.

* * * * *